Figure 1:
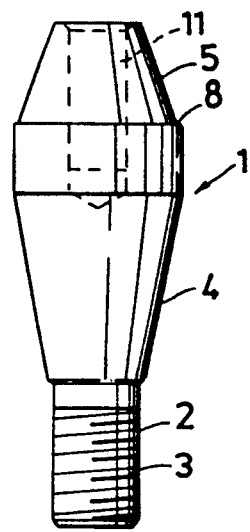

United States Patent [19]

Soderberg

[11] Patent Number: 5,009,596
[45] Date of Patent: Apr. 23, 1991

[54] DEVICE FOR FIXING A DENTAL PROTHESIS

[75] Inventor: Per O. Soderberg, Stockholm, Sweden

[73] Assignee: Astra Meditec Aktiebolag, Molndal, Sweden

[21] Appl. No.: 469,798

[22] Filed: Jan. 22, 1990

Related U.S. Application Data

[63] Continuation of Ser. No. 183,849, Apr. 20, 1988, abandoned.

[30] Foreign Application Priority Data

Apr. 22, 1987 [SE] Sweden ............................ 8701655

[51] Int. Cl.$^5$ .............................................. A61C 8/00
[52] U.S. Cl. .................................... 433/173; 433/174
[58] Field of Search ................ 433/173, 174, 175, 176

[56] References Cited

U.S. PATENT DOCUMENTS 4,631,031 12/1986 Richter ................................ 433/173
4,722,688 2/1988 Lonca ................................... 433/173

FOREIGN PATENT DOCUMENTS

WO85/02337 6/1985 PCT Int'l Appl. ................ 433/173
8504274 6/1987 Sweden .

OTHER PUBLICATIONS

T. Jemt, Modified Single and Short-Span Restorations Supported by Osseointegrated Fixtures in the Partially Edentulous Jaw, The Journal of Prosthetic Dentistry, Feb. 1986.

Primary Examiner—John J. Wilson
Attorney, Agent, or Firm—White & Case

[57] ABSTRACT

A device for fixing a dental prosthesis is described, which device as parts thereof comprises a spacing element (1) for anchoring into the jaw-bone of a patient and a socket (7) for fixing into a prosthetic part, whereby the socket will rest on the spacing element via an outer conical supporting surface (5) provided on one of said parts, which supporting surface will bear against an inner conical supporting surface (6) provided in the other of said parts. The device is characterized in that a shoulder or flange is provided on the part having the outer conical supporting surface, which shoulder or flange has a planar surface (8) oriented radially around the periphery of the supporting surface, and that an end surface (9) is provided on the part having the inner conical supporting surface oriented radially around the periphery of said supporting surface, whereby the planar surface (8) and the end surface (9) has such an axial position on the respective part that a fine parallel gap is formed between them on bearing of the supporting surfaces against each other. The gap enables checking of the correct bearing of the conical surfaces against each other.

2 Claims, 1 Drawing Sheet

DEVICE FOR FIXING A DENTAL PROTHESIS

This application is a continuation of application Ser. No. 183,849, filed on Apr. 20, 1988, now abandoned.

TECHNICAL FIELD

The present invention is related to a such device which primarily is intended for carrying a dental bridge or another rigid prosthetic part, for anchoring of the same to the jaw-bone of a patient at least two anchoring points, using at least two devices according to the invention. The device comprises a spacing element or pillar for fixing into the jaw-bone, preferably via an osseointegrated root element or implant, such as a threaded titanium screw, anchored into the jaw-bone, and a socket for fixing into the rigid prosthetic structure. The spacing element and the socket have conical supporting surfaces arranged to bear against each other on fixing of the prosthetic part to the jaw-bone.

STATE OF THE ART

A device as described above is previously known from WO85/02337. It has been found that a conical design of the bearing parts of the spacing element and the socket provides great advantages. Thus, it is easy to place the finished bridge or prosthesis into the oral cavity by the cones guiding the bridge into the correct position. Furthermore, a very stable anchoring of the bridge to the jaw-bone is achieved, while this could not always be achieved with older constructions. However, it has turned out that the bridge cannot always be built with sufficient precision due to several sources of defect during both preparatory model work and final preparation of the bridge. Thereby a defective fit occurs between the conical surfaces of the device at one or more anchoring points. This causes a substantial impairment of the carrying ability of the implant and may cause deformation and breakage of the rigid prosthetic part or of the parts carrying the same. Furthermore, saliva and bacteria may leak in between the pillar and the socket, causing a nucleus of bacteria which negatively affects the healing in of the implant. If this is discovered by the treating dentist the problem may be resolved by cutting the dental bridge and, after adjustment of the parts thereof to the positions of the pillars, again joining the parts, e.g. by soldering. However, it is very difficult for the dentist to discover the defective fit with previously known conical constructions. The present invention has the object of remedying this problem.

DESCRIPTION OF THE INVENTION

According to the present invention there is thus provided a device for fixing a dental prosthesis, which device as parts thereof comprises a spacing element for anchoring into the jaw-bone of a patient and a socket for fixing into a prosthetic part, whereby the socket will rest on the spacing element via an outer conical supporting surface provided on one of said parts, which supporting surface will bear against an inner conical supporting surface provided in the other of said parts. The device is characterized in that a shoulder or flange is provided on the part having the outer conical supporting surface, which shoulder or flange has a planar surface oriented radially around the periphery of the supporting surface, and that an end surface is provided on the part having the inner conical supporting surface, oriented radially around the periphery of said supporting surface, whereby the planar surface and the end surface has such an axial position on the respective part that a fine parallel gap is formed between them on bearing of the supporting surfaces against each other.

According to the invention there is thus achieved an externally visible control gap between the pillar and the socket in assembled position. If said gap is fine and parallel, this indicates that the conical supporting surfaces bear completely and correctly against each other. If, however, a broader and/or non-parallel gap is shown, this indicates that the conical supporting surfaces do not correctly bear against each other.

As described above, two or more devices according to the invention may be used for fixing of a dental bridge, which is part of a permanently attached prosthesis, which may only be released by the treating dentist. The device may however also be used for fixing of a bar (dolder bar) on which an overdenture, which may be released by the patient, may be attached by snap means or the like.

As evident from the above, by the spacing element being anchored into the jaw-bone it is usually understood that the spacing element is anchored via an osseointegrated root element. The spacing element may however be anchored into the jaw-bone by other means, for example by itself being osseointegrated therein.

In one of the spacing element and the socket the conical surface is an outer surface, and in the other it is an inner surface. According to a preferred embodiment of the invention the outer conical supporting surface, around the periphery of which the planar surface is provided on a shoulder or flange, is arranged on the spacing element, while the inner conical surface is arranged in the socket.

The fine parallel gap between the surfaces is obtained by giving that surface which is arranged around the conical outer surface an axial position at a point where the diameter of the conical outer surface is slightly greater than the diameter of the conical inner surface at the point where the end surface arranged thereto is positioned. The difference in diameter depends on the cone angle and may be calculated from a desired width of the gap. The lower limit for the width of the gap is governed by the same having to be greater than the added surface tolerance of the two surfaces. A usual surface tolerance for the parts is 20 $\mu$m, but a tolerance down to 5 $\mu$m may be achieved by available methods. The upper limit for the gap width is suitably about 200 $\mu$m.

Figure 2:
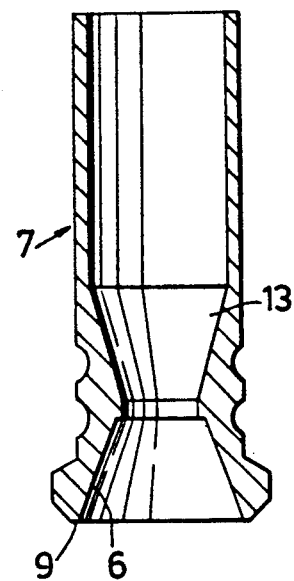
Figure 3:
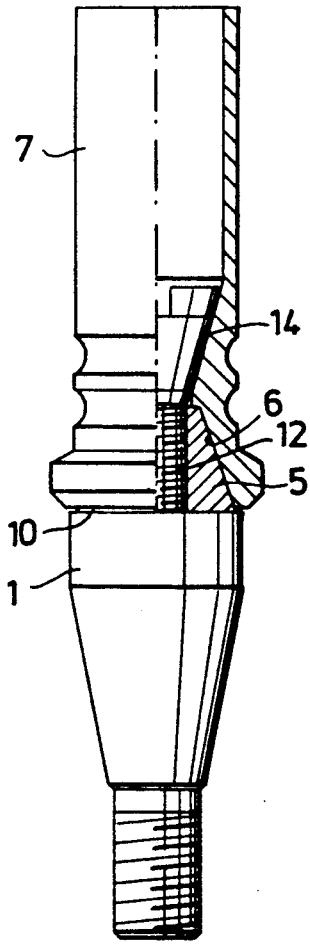
Figure 4:
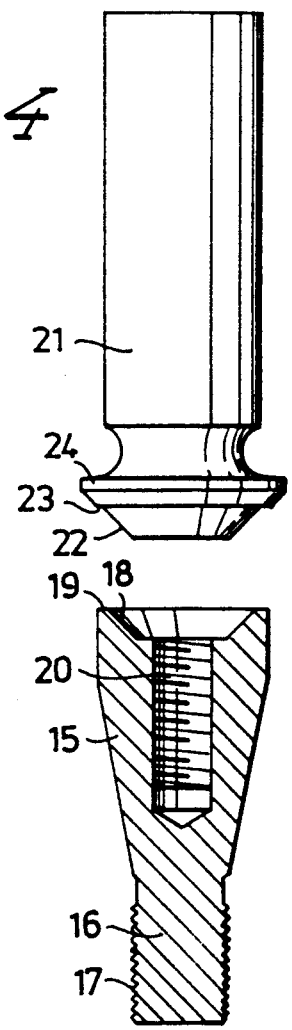

The invention is further described with reference to the appended drawings, where FIG. 1 is a side view of a spacing element according to one embodiment of the invention, FIG. 2 is a longitudinal section through a socket according to one embodiment of the invention, FIG. 3 shows the spacing element and the socket according to FIGS. 1 and 2 assembled in side view with the socket and the spacing element partly in section, and FIG. 4 is an exploded view showing a pillar and a socket according to an alternative embodiment of the invention.

In the drawings the spacing element is a pillar 1 which has a lower cylindrical portion 2 with threads 3 for attachment of the pillar in a manner known per se in a root screw or fixture anchored in the jaw-bone of a patient. The pillar has a downwardly tapering conical outer surface 4 arranged in a known manner to bear against a conical inner surface in the fixture. The upper end of the pillar has an outer conical supporting surface 5 at an angle of 70° against the radial plane, arranged to carry an inner conical supporting surface 6 in a socket 7. A planar annular control surface 8 is arranged radially on a shoulder around the periphery of the conical outer surface 5 of the pillar, and in a corresponding manner the end surface of the socket is shaped into a planar annular control surface 9 arranged radially around the periphery of the conical inner surface of the socket 6. A parallel fine gap 10 is formed between the control surfaces when the pillar 1 and the socket 7 are assembled and the conical supporting surfaces bear against each other. The pillar 1 has at its upper end an axial threaded hole 11 for attachment of a screw 12 which will bind together the pillar and the socket. The socket further has an inner upwardly widening conical inner surface 13 against which a conical head 14 of the screw 12, binding the pillar and socket together, will bear. Alternatively, the conical inner surface may be replaced by a planar screw seat against which a planar screw head will bear.

By 15 is denoted a pillar having a lower cylindrical part 16 with threads for attachment into a fixture. The pillar has in its upper part a conical depression having an inner conical supporting surface which at its widest portion connects to a radially oriented end surface 19. From the bottom of the conical depression an axial threaded hole 20 extends for attachment of a screw going through a socket 21, said screw to attach the socket to the pillar. The socket has a downwardly extending conical fitting part having an outer conical supporting surface 22. Around the broadest part of the supporting surface is arranged a planar annular control surface 23 in a radial plane of the socket. The control surface 23 is arranged on a flange 24. The control surface forms a narrow gap against the end surface 19 on correct bearing of the support surfaces against each other.

A suitable material for the pillar and the socket is titanium or a titanium alloy. However, other metals, such as stainless steel, may be used.

I claim:

1. A device for fixing a dental prosthesis, which device as parts thereof comprises a spacing element adapted for anchoring into the jaw-bone of a patient and a socket adapted for fixing into a dental prosthetic part, wherein the socket rests on the spacing element via an outer conical supporting surface provided on one of said parts, which supporting surface bears against an inner conical supporting surface provided in the other of said parts, characterized in that a shoulder is provided on the part having the outer conical supporting surface, which shoulder has a planer surface oriented radially around the periphery of the supporting surface, and that an end surface is provided on the part having the inner conical supporting surface, the end surface being oriented radially around the periphery of said supporting surface, and wherein the planar surface and the end surface have such an axial position on the respective part that an externally visible fine gap of uniform and predetermined thickness is formed between them on bearing of the supporting surfaces properly against each other, whereby an improperly formed gap provides a visible indication that the parts do not properly bear against one another.

2. A device according to claim 1, characterized in that the outer conical supporting surface is arranged on the spacing element, while the inner conical supporting surface is arranged in the socket.

* * * * *